United States Patent [19]

Lowe et al.

[11] Patent Number: 4,735,311
[45] Date of Patent: Apr. 5, 1988

[54] NEEDLE SHIELD ASSEMBLY

[75] Inventors: Allen D. Lowe, Montgomery; Homer J. Brown, Jr., Oreland; Arlington R. Harman, Frazer, all of Pa.

[73] Assignee: The West Company, Phoenixville, Pa.

[21] Appl. No.: 849,722

[22] Filed: Apr. 9, 1986

[51] Int. Cl.$^4$ .............................................. A61M 5/32
[52] U.S. Cl. ...................................... 206/365; 29/511; 264/249; 264/296; 604/198; 604/263
[58] Field of Search ..................... 29/509–511; 206/365; 264/249, 296; 604/192–198, 263

[56] References Cited

U.S. PATENT DOCUMENTS

| | | | |
|---|---|---|---|
| 2,219,301 | 10/1940 | Erhard | 29/511 |
| 2,400,722 | 5/1946 | Swan | 206/365 |
| 2,688,963 | 9/1954 | Smith | 604/192 |
| 2,972,991 | 2/1961 | Burke | 604/192 |
| 3,073,307 | 1/1963 | Stevens | 604/192 |
| 3,112,747 | 12/1963 | Cowley | 206/365 |
| 3,306,291 | 2/1967 | Burke | 206/365 |
| 3,380,448 | 4/1968 | Sadove et al. | 206/365 |
| 3,381,686 | 5/1968 | Pierce | 264/249 |
| 3,381,813 | 5/1968 | Coanda et al. | 206/365 |
| 3,390,759 | 7/1968 | Vanderbeck | 206/365 |
| 3,637,072 | 1/1972 | Narusawa et al. | 206/365 |
| 3,889,673 | 6/1975 | Dovey et al. | 206/365 |
| 4,215,087 | 7/1980 | Mathison | 264/296 |
| 4,248,246 | 2/1981 | Ikeda | 604/263 |
| 4,507,118 | 3/1985 | Dent | 604/263 |

FOREIGN PATENT DOCUMENTS

| | | | |
|---|---|---|---|
| 0227853 | 9/1959 | Australia | 206/365 |
| 0729419 | 3/1966 | Canada | 604/192 |
| 0868134 | 5/1961 | United Kingdom | 604/263 |

Primary Examiner—Jimmy G. Foster
Attorney, Agent, or Firm—Eugene E. Renz, Jr.

[57] ABSTRACT

A needle shield comprising an elongated tubular housing having a central bore, means at one end for detachably mounting the shield to the hub of a syringe assembly, and means defining an elongated generally cylindrical chamber in the end of the housing opposite the mounting means. An inner end communicates with the bore and an insert made of resilient impermeable pierceable material is snugly supported in the chamber. The chamber is of a diameter slightly greater than the diameter of the insert and includes a tapered wall portion at the inner end and has a section of smaller diameter than the insert to provide a tight generally hermetic sealing relation therewith. The wall of the chamber opposite the inner end is deformable to permit ease of assembly and deformation after insertion of the plug to firmly seat the plug in the chamber. The needle shield also includes a series of relief grooves in the exterior surface portion of the base of the housing which comprises the hub mounting portion to provide a degree of flexibility and ensure secure mounting even during expansion in autoclaving. The hub portion of the housing is also provided with a series of radially inwardly directed beads and ribs to provide sealing means between the hub of the needle shield and the needle hub.

3 Claims, 2 Drawing Sheets

NEEDLE SHIELD ASSEMBLY

BACKGROUND OF THE INVENTION

1. Field of the Invention

The present invention relates to improvements in shields or covers for parenteral needles and more specifically to one characterized by novel features of construction and arrangement providing ease of assembly to a needle and which is of relatively simplified construction so that it is easy and economical to manufacture.

2. Prior Art

Needle shields are not new per se. For example, DeLorenzo U.S. Pat. No. 2,831,483 shows a plastic shield having a mass of resilient material mounted in the tip end of the shield. Burke U.S. Pat. No. 3,370,588 shows a needle guard which is mounted in such a manner to provide a clearance between the tip of the needle and the top of the guard. Millet U.S. Pat. No. 4,249,530 shows a similar assembly. Garver, Sr. et al U.S. Pat. No. 4,402,682 also shows a plastic/rubber needle shield.

The process or method for assembling the resilient inserts in the needle shield housing shown in the prior art is time-consuming and difficult and does not lend itself readily to high-speed automated assembly equipment and techniques. Further, in these shield assemblies, the resilient insert is not locked axially against displacement in both directions as in accordance with the present invention. Locking the insert in a fixed position is important for proper penetration and seating of the needle tip.

Other patents of interest include the following:

| Inventor | Patent No. | Issue Date |
| --- | --- | --- |
| MacGregor | 1,331,271 | Feb. 17, 1920 |
| Jaros | 1,589,969 | June 22, 1926 |
| Saffir | 2,512,568 | June 20, 1950 |
| Saffir | 2,512,569 | June 20, 1950 |
| Hamilton | 2,933,087 | April 19, 1960 |
| Jacob | 3,186,408 | June 1, 1965 |
| Bradley et al | 3,390,678 | July 2, 1968 |
| Kitaj | 3,430,627 | March 4, 1969 |

SUMMARY OF THE INVENTION

With the foregoing in mind, it is an object of the present invention to provide a needle shield assembly which is easy and economical to manufacture and provide certain functional advantages over the prior art. For example, the assembly has sufficient resiliency to ensure retention on the hub of a syringe assembly even during autoclaving procedures. In one of the embodiments of the invention illustrated, a relief cut means is provided on the hub mounting section of the housing to allow slight expansion thereof while still retaining the desired locking effect. Further, the needle shield includes an elongated, tubular member made of a rigid plastic material having at one end an enlarged pocket for a rubber insert which is held firmly in place to provide a cushion penetrable by the hypodermic needle. The central channel in the housing is tapered so that the needle is guided during application of the cover. The rigid housing provides protection from injury when replacing the cover or using the cover to destroy the needle after use.

The needle shield is easy and economical to assemble. The distal end of the housing is normally straight sided and open providing a generally cylindrical pocket for the rubber insert. The insert is simply dropped into place and then by application of heat and pressure, the outer terminal edge of the pocket is simply rolled over to entrap the rubber insert in the pocket. The inner end of the pocket is slightly tapered or conical to provide a tight seal between the rubber insert at this juncture. In accordance with the preferred method of the present invention, the rubber insert is precompressed prior to the encapsulation by deforming the wall of the housing defining the insert pocket. This precompression is a factor ensuring hermetic sealing of the insert in the housing. Further, the frusto-conical configuration of the base of the pocket ensures a snug engagement with the insert after assembling and allows for a range of tolerance deviations with sacrificing the desired seal between the parts.

BRIEF DESCRIPTION OF THE DRAWINGS

These and other objects of the present invention and the various features and details of the operation and construction thereof are hereinafter more fully set forth with reference to the accompanying drawings, wherein.

DESCRIPTION OF THE PREFERRED EMBODIMENTS

Figure 1:
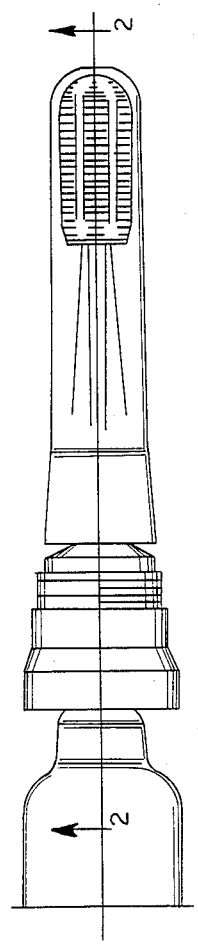
FIG. 1 is a fragmentary side elevational view of a needle shield in accordance with the present invention applied to the hub of a typical syringe assembly.
Figure 2:
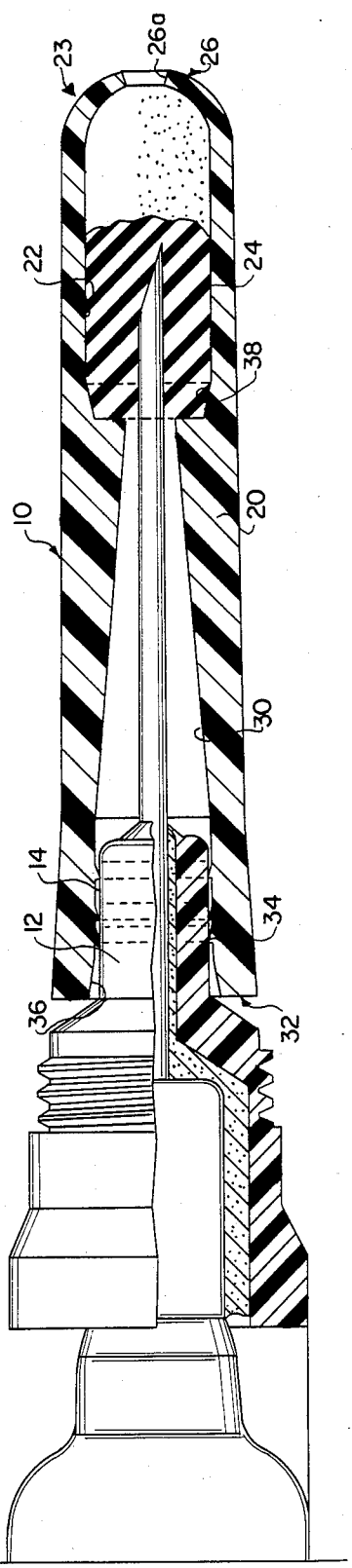
FIG. 2 is an enlarged fragmentary sectional view taken on lines 2—2 of FIG. 1 showing the interior details of the needle shield.
Figure 3:
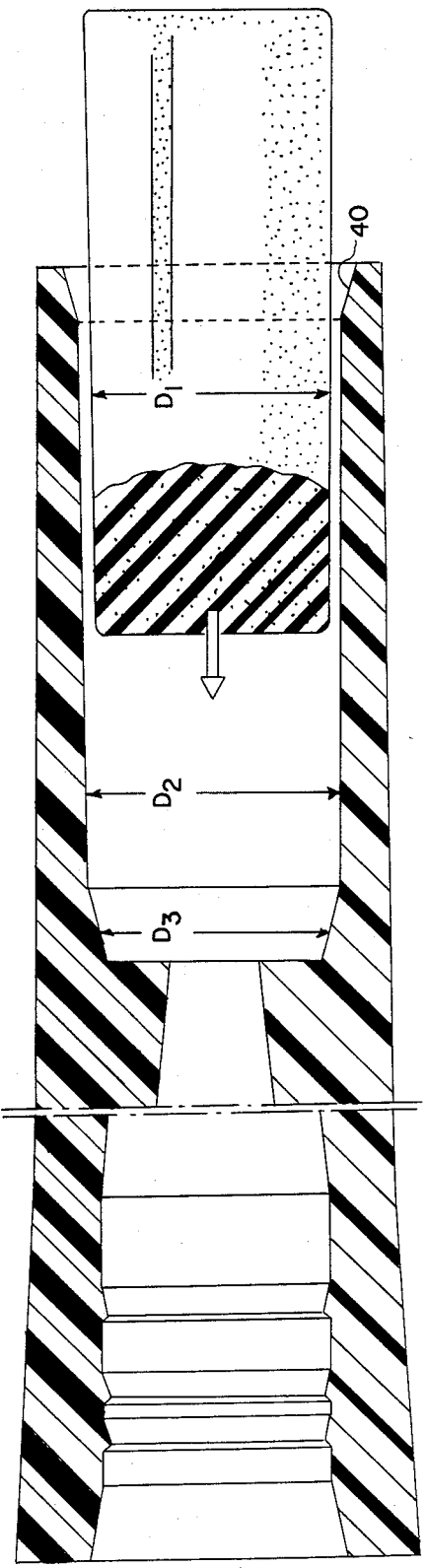
FIG. 3 is an enlarged fragmentary sectional view showing assembly of the elements of the needle shield.
Figure 4:
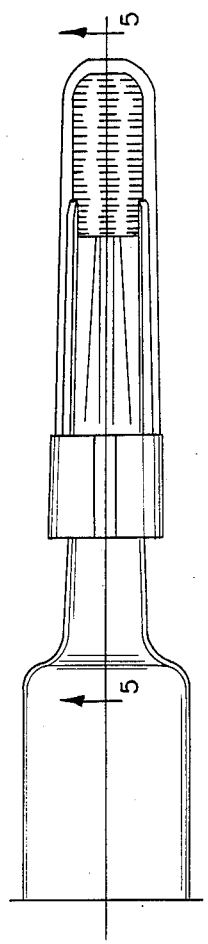
FIG. 4 shows a needle shield in accordance with the present invention as applied to another type of hub configuration of a hypodermic syringe.

Referring now to the drawings and particularly to FIGS. 1-3 thereof, there is illustrated a needle shield assembly in accordance with the present invention which is generally designated by the numeral 10. The needle shield illustrated is adapted for application to the hub 12 of a syringe assembly which is characterized by a relatively smooth outer cylindrical surface 14.

The needle shield which is preferably made of a rigid plastic material, such as polypropylene, comprises an elongated tubular housing 20 having a pocket 22 formed at one distal axial end 23 thereof which houses a rubber insert 24. As illustrated, the wall of the housing is rounded as at 26 at its outer terminal to form an enclosure for the insert as explained in more detail below. The pocket 22 communicates with an elongated central bore 30 which, as illustrated, is of tapered cross section and in the present instance, is radially inwardly convergent toward the insert end 23 of the housing. The open end 32 of the housing which fits over the needle hub 12, as illustrated, has a series of concentric ribs or ridges 34 which are axially spaced apart and an outwardly divergent pilot portion 36 adjacent the open end to facilitate application of the needle shield to the syringe assembly. As illustrated, the pocket 22 for the rubber insert 24 is of generally uniform diameter throughout its length. However, at the inner terminal end, the pocket 22 is slightly tapered inwardly as at 38 to provide a tight and effective seal after assembly of the insert 24.

Considering now the method of assembly of a needle shield in accordance with the present invention, the distal end 23 of the housing is generally cylindrical and defines an open chamber for insertion of the rubber insert. Note that the terminal edge of the housing walls defining the pocket are slightly beveled as at 40 to facilitate the forming operation. The insert 24, as illustrated, is initially of generally cylindrical configuration and has a uniform diameter throughout its length. The insert plug 24 is then positioned in the pocket as indicated by the arrow. The diameter $D_1$ of the insert is slightly less than the main diameter $D_2$ of the pocket 22 and greater than the smallest diameter $D_3$ of the tapered bottom of the pocket adjacent the central bore 30 of the housing. The insert 24 is simply dropped in place and then, by application of heat and pressure, the distal end of the housing is deformed to the shape shown in FIG. 2 to thereby encapsulate and seat the insert when the outer terminal edge is deformed and sets to the configuration shown. Before deformation in the manner described above, the insert 24 is precompressed by utilizing a precompression pin (not shown) which engages along the central axis of the insert through opening 26a (FIG. 2). Thus, while the pin is in place, the outer terminal wall of the housing is deformed and when the pin is withdrawn, the opening 26a is formed in the distal end of the opening. Further, the process adapts to high-speed automatic assembly equipment to produce assemblies having consistant hermetic seals.

Figure 6:
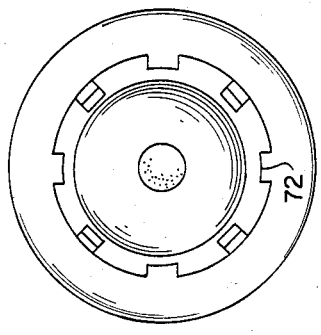
FIG. 6 is a top plan view of the embodiment of needle shield illustrated in FIG. 4.
Figure 5:
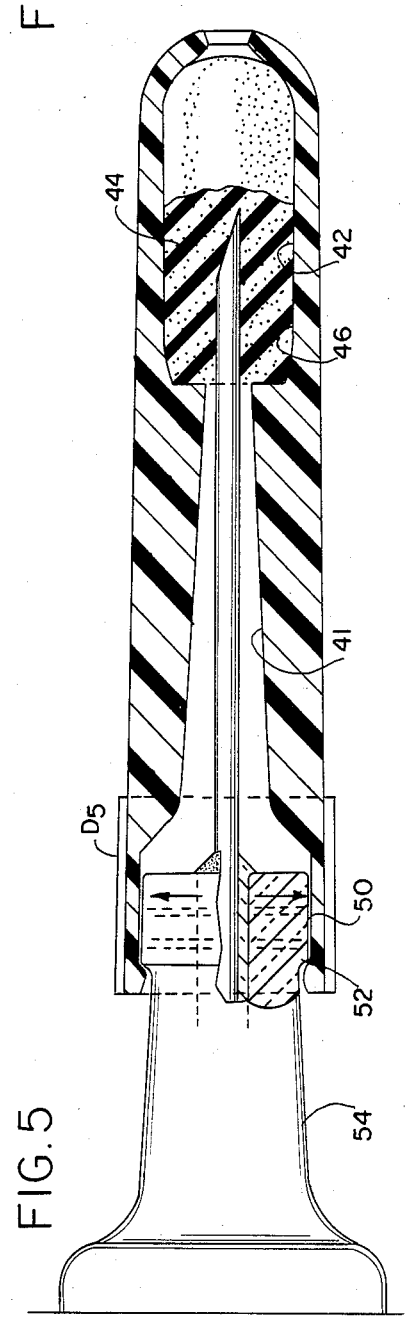
FIG. 5 is an enlarged fragmentary sectional view taken on lines 5—5 of FIG. 4.
Figure 7:
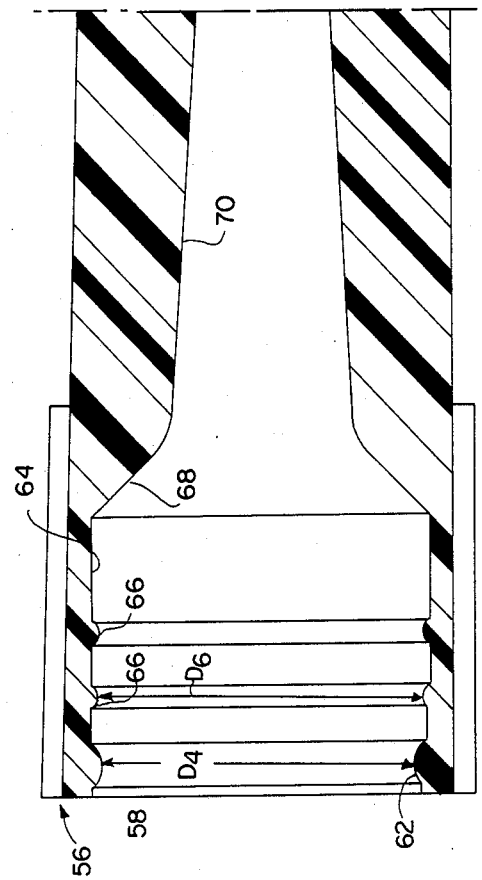
FIG. 7 is an enlarged framentary sectional view of the hub end of the needle shield.

FIGS. 4–7 inclusive show another form of needle shield in accordance with the present invention. The basic configuration of the housing and the insert are generally similar to that described in connection with the principal embodiment. Thus, the housing includes an elongated, tapered central bore 41 and the pocket 42 for insert 44 has a narrow, frusto-conical pocket section 46 to ensure a tight sealing fit when the rubber insert is assembled in essentially the same manner as described previously. In the present instance, the needle cover is adapted for application to a needle hub having a configuration illustrated in FIG. 5. Note that this needle hub has an enlarged head portion 50 defining a circumferentially extending shoulder 52 with the throat portion 54 of the syringe barrel. In this instance, the base end 56 of the housing is provided with a radially inwardly directed rib 58 adjacent its open terminal end which has an inner diameter $D_4$ smaller than the maximum diameter $D_5$ of the hub portion. The rib 58 is slightly beveled as at 62 to facilitate assembly of the bead over the needle hub. The interior wall of the base chamber 64 has, in the present instance, a series of concentric radially inwardly directed sealing beads 66 which are of a diameter $D_6$ slightly less than the diameter $D_5$ of the hub to snugly engage the same and provide a sealing fit therewith in the manner illustrated in FIG. 5. Note that the walls of the cylindrical chamber 64 terminate in a gently curved connecting wall 68 which merges with the tapered central bore 70 through which the needle passes upon application of the needle shield. As illustrated in FIG. 7, the inner diameter of beads 66 is greater than the inner diameter of rib 58 to provide good sealing and seating on the hub.

As illustrated in FIGS. 6 and 7, the hub mounting portion of the housing has a series of axially extending circumferentially equi-spaced grooves 72 which permit a degree of flexibility. By this arrangement, a tight mounting on the hub is ensured even during autoclaving procedures. These reliefs or keyways also compensate for any tolerances betweeen the hub and the sealing ribs 66.

A unitary forming tool comprising a dome-shaped pocket conforming to the finished rounded shape of the distal end of the housing and an axial pin projecting centrally of the dome may be utilized in the process for precompressing the insert and shaping the distal end of the housing.

While particular embodiments of the present invention have been illustrated and described herein, it is not intended to limit the invention and changes and modifications may be made therein within the scope of the following claims.

What is claimed is:

1. A needle shield comprising an elongated tubular housing having a central bore, means at one end for detachably mounting the shield to the hub of a syringe assembly, means defining an elongated generally cylindrical chamber in the end of said housing opposite the mounting means having an inner end communicating with said bore and an insert made of resilient impermeable pierceable material snugly supported in said chamber, said chamber being of a diameter slightly greater than the diameter of said insert and including a tapered wall portion at said inner end and having a section of smaller diameter than said insert to provide a tight generally hermetic sealing relation therewith, the wall of the chamber opposite said inner end being deformable to permit ease of assembly and deformation after insertion of the plug to firmly seat the plug in the chamber.

2. A needle shield comprising an elongated tubular housing having a central bore, means at one end for detachably mounting the shield to the hub of a syringe assembly having an enlarged head portion defining a circumferentially extending shoulder with a throat portion of the syringe barrel, means defining a chamber in the end of said housing opposite the mounting means communicating at its inner end with said bore and an insert made of resilient pierceable material snugly supported in said chamber, a series of relief grooves in the exterior surface portion of the base of the housing defining the hub mounting portion of the housing to provide a degree of flexibility and ensure secure mounting even during expansion in autoclaving procedures, means defining a radially inwardly directed rib at the free terminal opposite end of the housing of a diameter less than the diameter of the head portion of the hub to engage under the circumferentially extending shoulder and thereby support the needle shield in place when it is assembled over the hub and at least one radially inwardly directed sealing bead on the interior wall of the housing spaced upwardly from the free terminal opposite end thereof adapted to engage the side wall of the hub when it is mounted to provide a seal therewith, said bead being of an inner diameter greater than the inner diameter of said rib.

3. A method of making a needle shield consisting of the steps of forming an elongated tubular housing having a central bore and a generally cylindrical chamber at one axial end of the housing, inserting a generally cylindrical plug in the chamber, precompressing the plug and then deforming the end wall of the chamber to encapsulate the plug therein.

* * * * *